(12) United States Patent
Norton et al.

(10) Patent No.: US 8,426,343 B2
(45) Date of Patent: *Apr. 23, 2013

(54) METHOD OF IMPROVING GRASS QUALITY

(75) Inventors: Lawrence H. Norton, Bethlehem, PA (US); Richard K. Hanrahan, Englewood, NJ (US); David R. Spak, Cary, NC (US)

(73) Assignee: Bayer Cropscience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/237,104

(22) Filed: Sep. 20, 2011

(65) Prior Publication Data

US 2012/0122689 A1    May 17, 2012

Related U.S. Application Data

(63) Continuation of application No. 11/472,004, filed on Jun. 21, 2006, now Pat. No. 8,153,558, which is a continuation-in-part of application No. 11/237,371, filed on Sep. 28, 2005, now abandoned, which is a continuation-in-part of application No. 10/778,433, filed on Feb. 13, 2004, now abandoned.

(51) Int. Cl.
*A01N 55/02* (2006.01)
*A01N 43/46* (2006.01)

(52) U.S. Cl.
USPC .......................................... 504/191; 504/218

(58) Field of Classification Search ........................ None
See application file for complete search history.

(56) References Cited

U.S. PATENT DOCUMENTS

| | | | |
|---|---|---|---|
| 599,804 A | 3/1898 | Short | |
| 2,761,868 A * | 9/1956 | Lacey | 540/123 |
| 2,786,821 A | 3/1957 | Gardner et al. | |
| 2,870,037 A | 1/1959 | Converse et al. | |
| 4,634,555 A * | 1/1987 | Baxter et al. | 540/126 |
| 4,698,334 A | 10/1987 | Hoffiere et al. | |
| 4,737,515 A | 4/1988 | Hallenbach et al. | |
| 5,336,661 A | 8/1994 | Lucas | |
| 5,352,729 A | 10/1994 | Birkhofer et al. | |
| 5,599,804 A | 2/1997 | Mudge | |
| 5,643,852 A | 7/1997 | Lucas et al. | |
| 6,329,321 B2 | 12/2001 | Okura et al. | |
| 6,432,877 B2 | 8/2002 | Okura et al. | |
| 6,506,707 B1 * | 1/2003 | Bessette | 504/116.1 |
| 6,607,589 B2 * | 8/2003 | Adamic et al. | 106/31.49 |
| 7,431,743 B2 * | 10/2008 | Hughes | 8/506 |
| 2003/0194454 A1 * | 10/2003 | Bessette et al. | 424/745 |
| 2004/0192551 A1 * | 9/2004 | Bessette | 504/117 |
| 2005/0181949 A1 | 8/2005 | Norton et al. | |

FOREIGN PATENT DOCUMENTS

| | | |
|---|---|---|
| DE | 2511077 * | 9/1976 |
| DE | 2511077 A1 | 9/1976 |
| EP | 1563734 | 8/2005 |
| JP | 51096446 * | 8/1976 |
| JP | 3221576 * | 1/1990 |
| JP | 02250801 * | 10/1990 |
| JP | 03221576 | 9/1991 |
| JP | 3221576 | 9/1991 |
| JP | 06009323 | 1/1994 |
| JP | 06279162 * | 10/1994 |
| JP | 6279162 A | 10/1994 |
| JP | 09272818 | 10/1997 |
| JP | 10234231 | 9/1998 |
| JP | 11137084 | 5/1999 |
| JP | 11228859 | 8/1999 |
| JP | 11346576 | 12/1999 |
| JP | 2002293706 | 10/2002 |
| WO | 9312175 | 6/1993 |
| WO | 9632010 | 10/1996 |
| WO | 9632011 | 10/1996 |

OTHER PUBLICATIONS

1990 Turfgrass reports (effects of paint on spring greenup of Zoysiagrass and Effects of turf colorant and FeSO4 on spring greenup of Zoysiagrass), http://www.turf.uiuc.edu/research/summaries/1990/contents.html.
Younger, Victor, "Kikuyugrass, *Pennisetum clandestinum*, and Its Control", Southern California Turfgrass Culture, vol. 8, No. 1, 1958.
MSDS, Kannar: Turfkare Green, 2007.
MSDS, Kannar Green KC200, 2007.
Ben-Tal, Y. et al., "Effect of Chloro-Aluminum-Phthalocyanine on the Growth of *Lemna gibba* G3", J. Plant Physiol., vol. 135, p. 635-636, 1989, (abstract).
Kopeck, David et al., "Overseed Greens Performance Trials", 1995-1996.
Huang, Bingru, "Better creeping bentgrass through electricity", GCM, 2003, p. 85-86.
Liu, Xiaozhong et al., "Cytokinin Effects on Creeping Bentrgrass Responses to Heat Stress: I. Shoot and Root Growth", Crop Sci., vol. 42, p. 457-465, 2002.
Huang Bingru et al., "Physiological Responses of Creeping Bentgrass to Heat Stress Affected by Phosphonate Fungicide Application", International Turfgrass Society, Research Journal vol. 11, 2009, pp. 799-806.
Ben-Tal, Y. et al., "Effect of Chloro-Aluminum-Phthalocyanine of the Growth or *Lemna giffa* G3", Jourcan of Plant Physiology, col. 135, No. 5., 1989, pp. 635-636, XP009047422.
Van Haeringen et al., "The Development of Solid Spectral Filters for the Regulation of Plant Growth", Photochemistry and Photobiology, vol. 67, No. 4, 1998, pp. 407-413, XP009047423.
Printout of http://www2.siri.org/msds/f2/bzz/bzzsc.html, for ingredients in Rohm and Haas Co.'s FORE.TM. Fungicide, 62440 (1991).
Tal et al.,"Effect of Chloro-Aluminum-Phthalocyanine on the Growth of *Lemna gibba* G3", J. Plant Physiol., 1989, vol. 135, pp. 635-636.

(Continued)

*Primary Examiner* — Alton Pryor (57) ABSTRACT

The invention relates to a method of improving grass quality comprising applying an effective amount of a composition containing a phthalocyanine to the grass in the substantial absence of phosphorous acid, monoalkyl esters of phosphorous acid, or salts thereof.

12 Claims, 12 Drawing Sheets

OTHER PUBLICATIONS

Merck Index, 11 edition, Entry 2515—Copper Phthalocyanine, 1989.
Cleary, Label & MSDS Guide, http://www.clearychemical.com/labelsindex.html, pp. 2-4, indicated as being effective on Oct. 1997.
Odoc, Contents of 1990 Turfgrass Reports, http://web.archive.org/web/20020, pp. 1-2, 1990.
Appleyard Lees, "Heat stress study using Greenzit pigment", pp. 3-7, dated Nov. 1, 2011.
Cleary Chemical Corporation, "Use of Cleary's Grass Greenzit", p. 1, Technical Information, 2004.
Deformulation of RD 7212 Grass Greenzit, pp. 1-5, cited on p. 2 of the Opposition Decision for Patent No. EP-B-1-563 734, dated Nov. 29, 2011.
Quantification of phosphorous in water based green pigments, p. 1, cited on p. 2 of the Opposition Decision for Patent No. EP-B-1-563 734, dated Nov. 29, 2011.
"Turf grass coloration using hexadentate cobalt phthalocyanine amine complex salts", AN-1976-74211X[40], p. 1, 1975.
Grass Greenzit specimen label, pp. 1-2, indicated as being effective on Jan. 1, 1998.
Van Haeringen, C. J. et al., "The Development of Solid Spectral Filters for the Regulation of Plant Growth", Photochemistry and Photobiology, vol. 67, No. 4, p. 407-413, (abstract), indicated as being accepted on Jan. 13, 1998 and published online on Jan. 2, 2008.
A Guide to NTEP Turfgrass Ratings, prepared by: Kevin Morris, http://www.ntep.org/reports/ratings.htm, pp. 1-4, dated Nov. 4, 2011.
Van Dam, John et al.; "A Turfgrass Colorant Study"; California Turfgrass Culture, vol. 21, No. 3, 1971.
Kannar Product Turf Enhancing Products, http://web.archive.org/web/20040101182326/http://kannarcom/; dated 2004.
Opposition Decision for Patent No. EP-B-1-563 734, pp. 1-33, Nov. 29, 2011.
K.L. Diesburg, "Effects of Turf Colorants and FES04 on Spring Greenup of Zoysiagrass", pp. 1-2, dated 1990, and available at http://www.turf.uiuc.edu/research/summaries/1990/effect_colorant.pdf.
English Translated Office Action for Appeal No. 2011-17402 for Japanese Patent Application No. 2005-20775 mailed Dec. 18, 2012.

* cited by examiner

METHOD OF IMPROVING GRASS QUALITY

RELATED APPLICATIONS

This application is a Continuation of U.S. application Ser. No. 11/472,004, filed Jun. 21, 2006, which is a Continuation-In-Part of U.S. application Ser. No. 11/237,371, filed Sep. 28, 2005, now abandoned, which is a Continuation-In-Part of U.S. application Ser. No. 10/778,433, filed Feb. 13, 2004, now abandoned, the entire contents of which are hereby incorporated by reference in its entirety.

BACKGROUND OF THE INVENTION

The present invention relates to methods of improving quality of grass, particularly turfgrass, and relieving stress on grass and to compositions suitable therefor.

Phthalocyanines are known pigments having many applications, such as colorants for inks and coatings and even for turfgrass paints. E.g., DE 2,511,077 and JP 03/221576. Copper phthalocyanine has been used, but only in combination with certain other active ingredients, for enhancing turf quality. For example, U.S. Pat. No. 5,599,804 describes a method of combating fungi and enhancing turf quality in turfgrass by applying in specific ratios certain phthalocyanines in combination with phosphorous acid or an alkaline earth metal salt thereof or with certain monoester salts of phosphorous acid. U.S. Pat. No. 5,643,852 describes a method of enhancing turf quality in turfgrass by applying in specific ratios certain phthalocyanines in combination with (i) phosphorous acid or an alkaline earth metal salt thereof or certain monoester salts of phosphorous acid and (ii) certain ethylene bisdithiocarbamate contact fungicides. U.S. Pat. No. 5,336,661 describes a method of treating bentgrass and enhancing turf quality by applying in specific ratios (i) certain monoester salts of phosphorous acid and (ii) a metallic ethylene bisdithiocarbamate contact fungicide. This patent also describes a specific composition containing a combination of aluminum tris(O-ethylphosphonate) (fosetyl-al) and a manganese-zinc ethylene bisdithiocarbamate complex (mancozeb) used in a form (i.e., FORE fungicide) believed to have contained an unknown amount of the phthalocyanine compound Pigment Blue 15.

It has now unexpectedly been found that the quality of grass, including turfgrass, can be improved by applying certain phthalocyanines in the substantial absence of the additional components mentioned above and at application rates that are lower than those typically used for coloring turfgrass.

SUMMARY OF THE INVENTION

The present invention provides a method of improving grass quality comprising applying an effective amount of a composition containing a phthalocyanine to the grass, with the proviso that the composition does not include an effective amount of phosphorous acid or a salt thereof or of monoalkyl esters of phosphorous acid or salts thereof and preferably also does not include metallic ethylene bisdithiocarbamate contact fungicides or other fungicides.

The present invention further provides a composition for improving grass consisting essentially of an effective amount of a grass-improving amount of a phthalocyanine, at least one dispersant acceptable for use with grass, at least one carrier acceptable for use with grass, and, optionally, water.

DETAILED DESCRIPTION OF THE INVENTION

Suitable phthalocyanines for use according to the invention include metal-free phthalocyanines or metal-containing phthalocyanines. The metals of metal-containing phthalocyanines are typically transition metals such as copper, silver, gold, zinc, cadmium, mercury, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, and platinum. Copper, nickel, cobalt, iron, and zinc phthalocyanines are preferred, with copper phthalocyanines being particularly preferred.

Suitable substituted phthalocyanines include phthalocyanines substituted from 1 to 4 times on each isoindole group independently. Examples of suitable substituents for the isoindole groups of phthalocyanines include but are not limited to halogen, unsubstituted or substituted lower alkyl, lower alkoxy, alkylamino, alkylthio, ammonium, sulfonato, sulfonato alkyl, sulfate, phosphate, phosphonate, and carboxylate. The ionic or ionizable substituents can have as counterions the alkali metals, preferably lithium, sodium, or potassium, the alkaline earth metals, preferably beryllium, magnesium, calcium, strontium, or barium, or various ammonium ions. By the terms lower alkyl and lower alkoxy are generally meant alkyl groups of from 1 to 6 carbon atoms and alkoxy groups of from 1 to 6 carbon atoms. Particular preferred substituted phthalocyanines are copper phthalocyanines that are multiply substituted with chlorine atoms.

Suitable phthalocyanines are commercially available and include but are not limited to Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7. In one preferred embodiment, the phthalocyanine is Pigment Blue 15, which is the unsubstituted copper phthalocyanine also known as phthalocyanine blue. In another preferred embodiment, the phthalocyanine is Pigment Green 7, which is a polychlorinated copper phthalocyanine.

The compositions used according to the invention do not include effective amounts of phosphorous acid, monoalkyl esters of phosphorous acid, or salts thereof. Examples of such compounds to be excluded or substantially excluded are (i) compounds of the formula $[HP(OR)O_2)^-]_n M^{m+}$ in which R is $C_2$-$C_4$ alkyl, M is an alkali metal, alkaline earth, or aluminum atom, and n is an integer of from 1 to 3 equal to the valence of M, or (ii) phosphorous acid or alkaline earth metal salts thereof.

Other compounds are also preferably excluded or substantially excluded from the present invention. For example, in one preferred embodiment, the compositions and methods of the invention do not include effective amounts of (i) phosphorous acid, monoalkyl esters of phosphorous acid, or salts thereof and (ii) metallic ethylene bisdithiocarbamate contact fungicides, especially manganese ethylene bisdithiocarbamate or manganese-zinc ethylene bisdithiocarbamate. In a second preferred embodiment, the compositions and methods of the invention do not include effective amounts of (i) phosphorous acid, monoalkyl esters of phosphorous acid, or salts thereof, (ii) the metallic ethylene bisdithiocarbamate contact fungicides mentioned above, and (iii) one or more other fungicides, particularly those selected from the group consisting of basic salts or hydroxides of copper (e.g., the oxychloride or oxysulfate), (tetrahydro)phthalimides (e.g., captan, captafol, or folpel), methyl (butylcarbamoyl)-2-benzimidazolecarbamate (benomyl), thiophanates such as dimethyl (1,2-phenylene)bis(iminocarbonothioyl)bis(carbamate) (thiophanate-methyl), tetrachloroisophthalonitrile (chlorothalonil), 3-(3,5-dichlorophenyl)-N-(I-methylethyl)-2,4-dioxo-I-imidazolidinecarbox-amide (iprodione), 1-[2-(2,4-dichlorophenyl)-4-propyl-1,3-dioxolan-2-yl methyl-IH-1,2,4-triazole (propiconazole), 1-(4-chlorophenoxy)-3,3-dimethyl-I(IH-1, 2,4-triazol-1-yl)-2-butanone (triadimafon), 2-hydroxy-1,3,2-dioxaphospholanes, and β-hydroxyethyl phosphites. In a third preferred embodiment, the compositions of the invention do not include effective amounts of the components (i) and (iii) mentioned above.

The compositions used according to the invention preferably consist essentially of an effective amount of a phthalocyanine (preferably Pigment Blue 15 and more preferably Pigment Green 7) and more preferably consist of an effective amount of a phthalocyanine (preferably Pigment Blue 15 and more preferably Pigment Green 7), at least one dispersant, at least one carrier, and, optionally, water. The compositions may in one embodiment contain the phthalocyanine and water with no carrier. The compositions of the invention may consist essentially of a phthalocyanine compound and water. The compositions may also consist of a phthalocyanine compound and water.

The compositions according to the instant invention generally contain from about 0.5 to about 95% of phthalocyanine by weight, preferably from 1% to 50%, more preferably from 2% to 35%. The remainder of the composition up to 100% comprises a carrier as well as various optional additives such as those hereafter indicated.

By "carrier" there is meant herein an organic or inorganic material, which can be natural or synthetic and which is associated with the phthalocyanine and facilitates its application to the locus to be treated. This carrier is thus generally inert and should be agriculturally acceptable, especially on the contemplated or treated grass. The carrier can be solid (e.g., clay, silicates, silica, resins, wax, fertilizers, or the like) or liquid (e.g., water, alcohols, ketones, oil solvents, saturated or unsaturated hydrocarbons, chlorinated hydrocarbons, liquefied petroleum gas, or the like).

Among the many optional additives suitable for use in compositions of the invention include surfactants and other ingredients, such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments (other than those contemplated as an active ingredient for purposes of the invention), and polymers.

More generally, the compositions of the invention can include all kinds of solid or liquid additives which are known in the art of crop protection and horticultural pest control treatments.

The surfactants can be of the emulsifying or wetting type and can be ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. When the spraying vehicle is water, the use of at least one surfactant is generally required because the active ingredients are not water-soluble.

Dusting powders, granulates, solution, emulsifiable concentrates, emulsions, suspended concentrates and aerosols are also contemplated within the invention. The wettable powders according to the invention can be prepared in such a way that they contain from 1% to 95% by weight of the active material, and they normally contain, in addition to a solid support, from 0 to 5% by weight of a wetting agent, from 3 to 10% by weight of a dispersant, and, when necessary, from 0 to 10% by weight of one or more stabilizers and/or other additives, such as penetration agents, adhesives or anti-clumping agents, or colorants. The compositions according to the invention can contain other ingredients, for example protective colloids, adhesives or thickeners, thixotropic agents, stabilizers or sequestrants, as well as other active materials known to have pesticidal properties, especially certain fungicides, acaricides, and insecticides.

The present invention can be practiced on all grasses, including those used for lawns or other ornamental purposes, such as turfgrass, and those used as food or to produce grain for human or animal consumption. Some grasses, such as rye grasses, can be used both for food and for esthetic purposes. It is particularly preferred to practice the invention on turfgrasses, which are typically characterized as cool season turfgrasses and warm season turfgrasses. Examples of cool season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.), and bulbous bluegrass (*Poa bulbosa* L.); the bentgrasses and redtop (*Agrostis* spp.), such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.); the fescues (*Festucu* spp.), such as red fescue (*Festuca rubra* L. spp. rubra), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.), meadow fescue (*Festuca elanor* L.); the ryegrasses (*Lolium* spp.), such as annual ryegrass (*Lolium* multiflorum Lam.), perennial ryegrass (*Lolium perenne* L.), italian ryegrass (*Lolium multiflorum* Lam.); and the wheatgrasses (*Agropyron* spp.), such as fairway wheatgrass (*Agropyron cristatum* (L.) Gaertn.), crested wheatgrass (*Agropyron desertorum* (Fisch.) Schult.), and western wheatgrass (*Agropyron smithii* Rydb.). Other cool season turfgrasses include beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.). Examples of warm season turfgrasses include Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool season turfgrasses are generally preferred for treatment according to the invention. More preferred is bluegrass, bentgrass and redtop, fescue, and ryegrass. Bentgrass is most preferred. Examples of grasses that are useful as crops include corn or maize (*Zea mays*), sorghum (*Sorghum sudanense*), switchgrass (*Panicum virgatum*), millet (*Panicum miliaceum*), rice (*Oryza* spp.), wheat (*Triticum* spp.), oats (*Avena* spp.), barley (*Hordeum* spp.), and rye (*Secale cereale*).

In general the rate of application at the locus is from 0.001 to 10 kilograms of phthalocyanine per hectare (kg/ha), preferably from about 0.01 to about 2 kg/ha, more preferably from about 0.1 to about 1 kg/ha, most preferably from about 0.2 to about 0.8 kg/ha. The compositions of the invention are applied by known methods.

The following examples further illustrate details for the method and compositions of this invention. The invention, which is set forth in the foregoing disclosure, is not to be limited either in spirit or scope by these examples. Those skilled in the art will readily understand that known variations of the conditions of the following procedures can be used.

EXAMPLES

Example 1

The following test methods were used to compare the effectiveness of a phthalocyanine composition according to the invention with known compositions. The following compositions were used in the experiments: Pigment Green 7 obtained from Sun Chemical Corporation as the water-dispersible product SUN T-64-1660 (containing 45 to 55 wt. % of Pigment Green 7) was used alone. A mixture of Pigment Green 7 and fosetyl-al was used as the commercially available product Chipco® Signature™ fungicide from Bayer Environmental Science, Montvale, N.J. The compound fosetyl-al was used as Chipco® Aliette® WDG fungicide available from Bayer Environmental Science, Montvale N.J.

Seeds of "Penncross" creeping bentgrass were sown in polyvinyl chloride (PVC) tubes (10 cm in diameter and 20 cm in length) filled with coarse sand. Plants were kept in a growth chamber for 90 days before treatment stated to allow root and canopy establishment. The daily temperature in the growth chamber was 20/16° C., the photosynthetic photon flux density was 400 µmol m$^{-2}$ s$^{-1}$, and the photoperiod was 12 hours/day. Turf was mowed twice weekly at 4 mm with scissors, irrigated every other day until there was free drainage from the bottom of tubes, and fertilized weekly with 40 ml full-strength Hoagland's nutrient solution (Hoagland and Arnon, 1950). Insecticide was applied to kill whitefly when necessary.

Two treatments were conducted in the experiment. A high temperature treatment was maintained at 35/30° C. (day/night temperatures) and an optimum temperature treatment of 20/16° C. was used as temperature control. Signature fungicide and Aliette fungicide were each applied to the foliage in each treatment biweekly at the rate of 4 oz./1000 sq. ft. (ca. 1.3 mL/m$^2$) for Signature fungicide and Aliette fungicide; and Pigment Green 7 was applied as an aqueous dispersion sprayed on the foliage in each treatment biweekly at the rate of 6.92 g/1000 sq. ft. (ca. 0.74 kg/ha), in order to roughly approximate the amount of phthalocyanine being applied in each plot. Water alone was used as a non-fungicide control. (Treatments were applied only to plants at high temperature and not to control plants.) When treatments started, half of plants were sprayed 4 weeks before the high temperature treatment (i.e., as a pretreatment) and half of plants were sprayed at the same time of high soil temperature started (i.e., no pretreatment). Each treatment had 5 replications.

Measurements were made at 1 week after treatments were applied. Turf quality was visually rated at the scale from 0 to 9 according to the density, greenness, and uniformity of the grass, with 0 being the worst and 9 being the best.

Canopy net photosynthetic rate was measured as described below using a Li-6400 portable photosynthesis system (available from LiCor, Lincoln, Nebr.).

For determination of the biomass, samples of shoots and roots at the end of each experiment were cleaned and dried at 80° C. in an oven for 72 hours. The dry weight of shoots and roots were used to indicate biomass of shoots and roots.

Chlorophyll and carotenoids were extracted by soaking 50 mg fresh shoots in 20 ml dimethyl sulfoxide (DMSO) in the dark for 72 hours. Absorbance of each extractant at 663 nm, 645 nm, and 470 nm was used to determine chlorophyll content using the formula of Arnon (1949) and carotenoids content using the formula of Lichtenthaler and Wellburn (1983) Canopy photochemical efficiency was estimated by measuring chlorophyll fluorescence (Fv/Fm) using plant photosynthesis efficiency analyzer (available from ADC Bioscientific Limited, Herts, England).

Root mortality was measured using the method of Knievel (1973) with modification. Samples of 0.5 g clean fresh roots were incubated with 10 mL 0.6% 2,3,5-triphenyltetrazolium chloride (in 0.05 M phosphate buffer, pH 7.4) for 24 hours in the dark at 30° C. Roots were then rinsed twice with deionized water. Formazan was extracted from roots twice with 95% ethanol at 70° C. for 4 hours. The combined extractant from the two extractions was adjusted to a final volume of 20 mL with 95% ethanol. Absorbance at 490 nm was used to determine root mortality.

Test Results

A. Turf Quality

Figure 1:
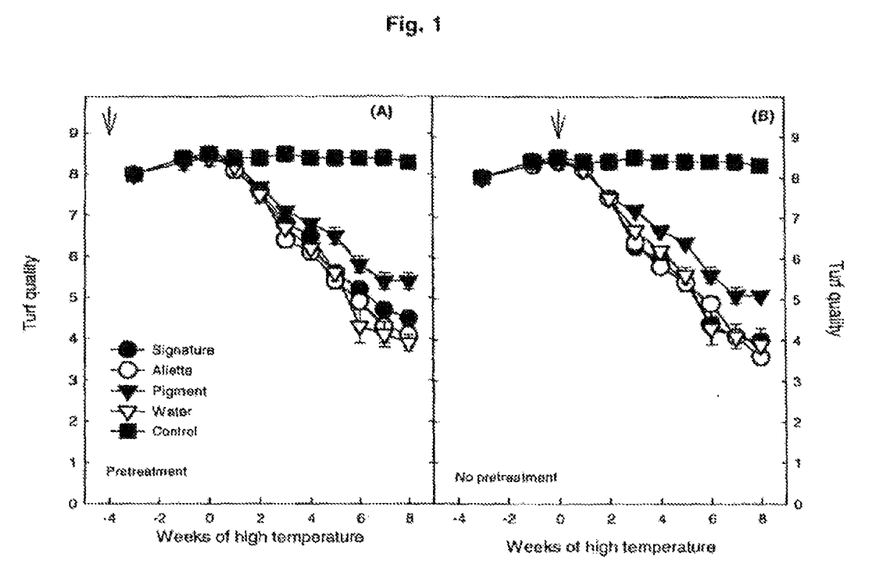
FIG. 1 illustrates the effect of phthalocyanine and fungicide applications on Penncross creeping bentgrass turf quality at high temperature treatment.

FIG. 1 illustrates the effect of fungicide application on Penncross creeping bentgrass turf quality at high temperature treatment. Data are shown as mean±sd. Arrow indicates the date of first fungicide application.

The quality of plants at the control temperature was maintained at high level during the entire experimental period (FIG. 1). Heat stress reduced turf quality beginning 2 weeks after high temperature. For the plants with pretreatment (FIG. 1), turf quality was highest at the application of Pigment Green 7, followed by application of Signature fungicide and Aliette fungicide, water application showing the lowest turf quality. For the plants without pretreatment (FIG. 1B), application of Pigment Green 7 showed higher turf quality than applications of Signature fungicide, Aliette fungicide, and water. Plants with pretreatment showed higher turf quality than those plants without pretreatment (cf. FIGS. 1A and 1B).

B. Net Photosynthetic Rate (Pn)

Figure 2:
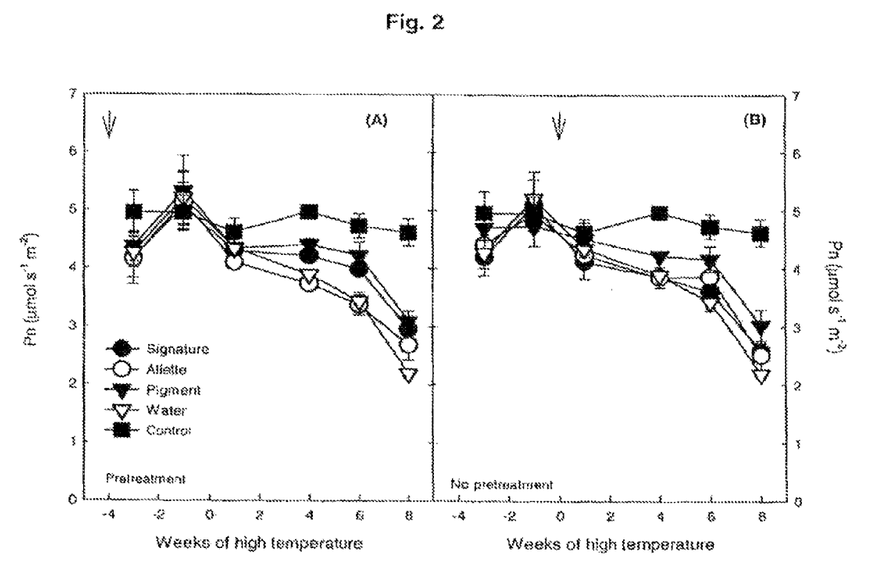
FIG. 2 illustrates the effect of phthalocyanine and fungicide applications on net photosynthetic rate of Penncross creeping bentgrass at high temperature treatment.

FIG. 2 illustrates the effect of fungicide application on the net photosynthetic rate (Pn) of Penncross creeping bentgrass at high temperature treatment. Data are shown as mean±sd. The arrow indicates the date of first fungicide application.

High temperature decreased canopy Pn beginning 4 weeks after heat stress (FIGS. 2A and 2B). For the plants with fungicide pretreatment, Pn was higher with application of Pigment Green 7 and Signature fungicide than with application of Aliette fungicide and water (FIG. 2A). For the plants without pretreatment, Pn was highest at phthalocyanine application, lowest at water application, and intermediate with application of Signature fungicide and Aliette fungicide (FIG. 2B). Pn was higher for plants with pretreatment than for those without pretreatment (FIGS. 2A and 2B).

C. Chlorophyll Content

Figure 3:
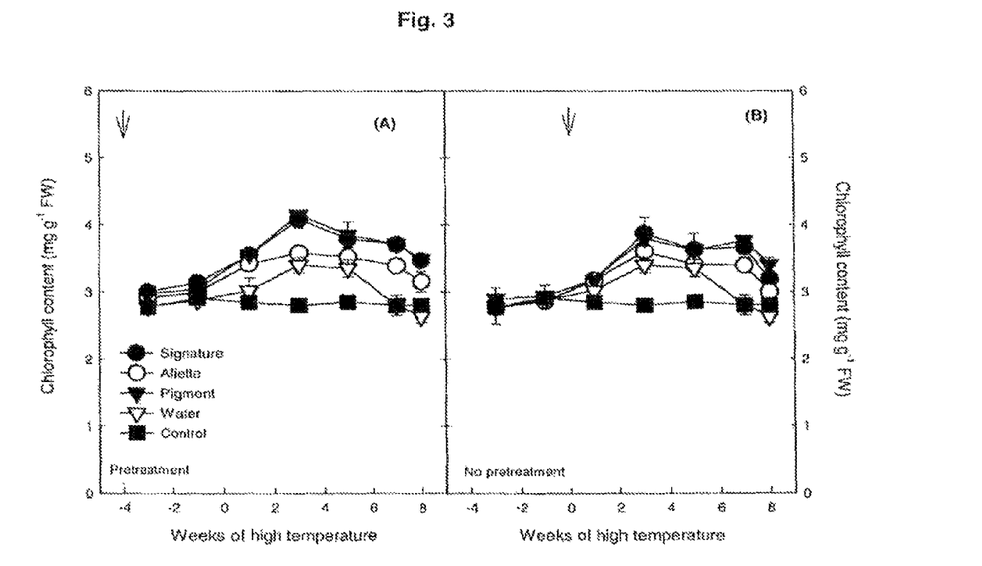
FIG. 3 illustrates the effect of phthalocyanine and fungicide applications on chlorophyll content of Penncross creeping bentgrass at high temperature treatment.

FIG. 3 illustrates the effect of fungicide application on the chlorophyll content of Penncross creeping bentgrass at high temperature treatment. Data are shown as mean±sd. The arrow indicates the date of first fungicide application.

Chlorophyll content in the fresh weight basis increased at high temperature treatment (FIGS. 3A and B). For plants with pretreatment, chlorophyll content was highest with application of Signature fungicide and Pigment Green 7, lowest at water application, and intermediate with application of Aliette fungicide (FIG. 3A). For plants without fungicide pretreatment, chlorophyll content was higher with application of Signature fungicide and Pigment Green 7 than with application of Aliette fungicide (FIG. 3B). Chlorophyll content was higher for plants with pretreatment than for those without pretreatment (FIGS. 3A and 3B).

D. Photochemical Efficiency (Fv/Fm Ratio)

Figure 4:
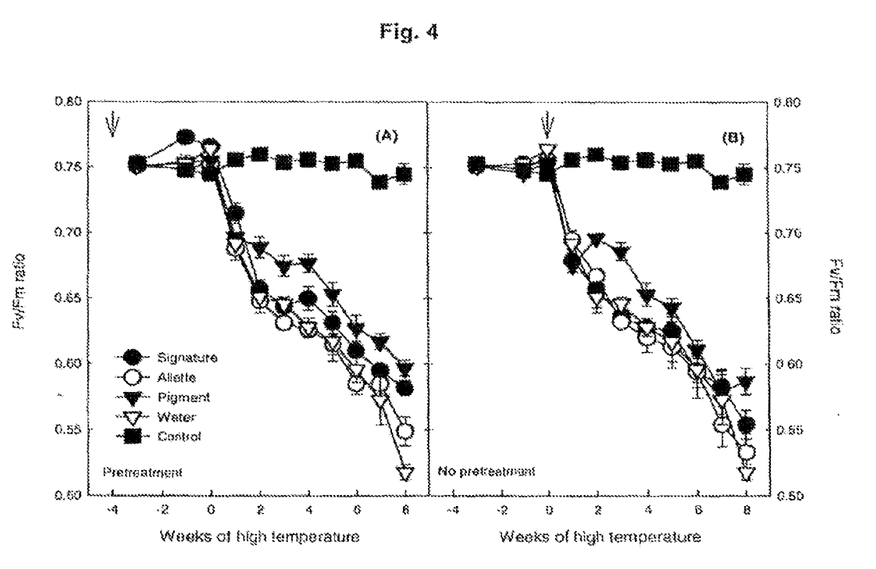
FIG. 4 illustrates the effect of phthalocyanine and fungicide applications on chlorophyll photochemical efficiency of Penncross creeping bentgrass at high temperature treatment.

FIG. 4 illustrates the effect of fungicide application on the chlorophyll photochemical efficiency (Fv/Fm) of Penncross creeping bentgrass at high temperature treatment. Data are shown as mean±sd. The arrow indicates the date of first fungicide application.

Photochemical efficiency (Fv/Fm) declined beginning 1 week after high temperature treatment (FIGS. 4A and 4B). For the plants with and without fungicide pretreatment, Fv/Fm was highest at application of Pigment Green 7, followed by application of Signature fungicide, Aliette fungicide, and water. Fv/Fm was higher for the plants with pretreatment than for those without pretreatment.

E. Carotenoids Content

Figure 5:
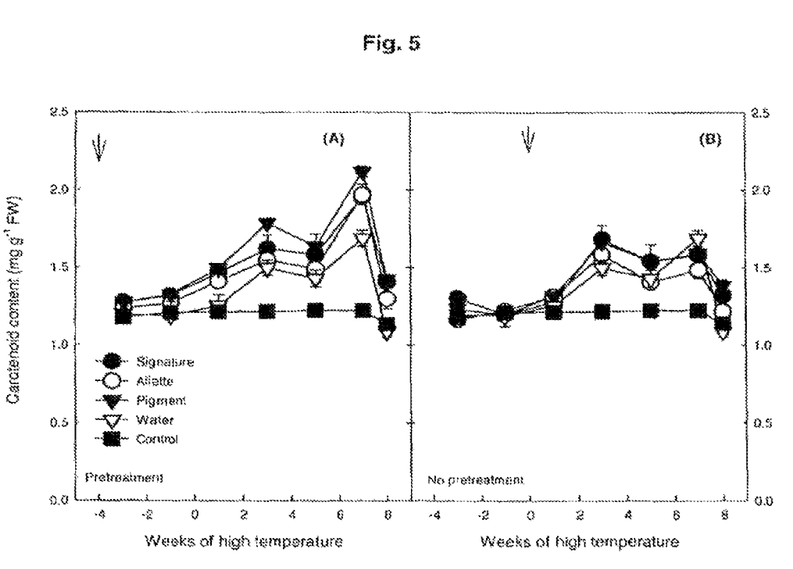
FIG. 5 illustrates the effect of phthalocyanine and fungicide applications on carotenoids content of Penncross creeping bentgrass at high temperature treatment.

FIG. 5 illustrates the effect of fungicide application on the carotenoids content of Penncross creeping bentgrass at high temperature treatment. Data are shown as mean±sd. The arrow indicates the date of first fungicide application.

Carotenoids content increased in high temperature treatment (FIGS. 5A and 5B). For the plants with or without pretreatment, carotenoids content was higher with application of Signature fungicide and Pigment Green 7 than with application of Aliette fungicide and water (FIG. 5A). Carotenoids content was higher in plants with pretreatment than for those without pretreatment (FIGS. 5A and 5B).

F. Shoot Growth Rate in Canopy Height

Figure 6:
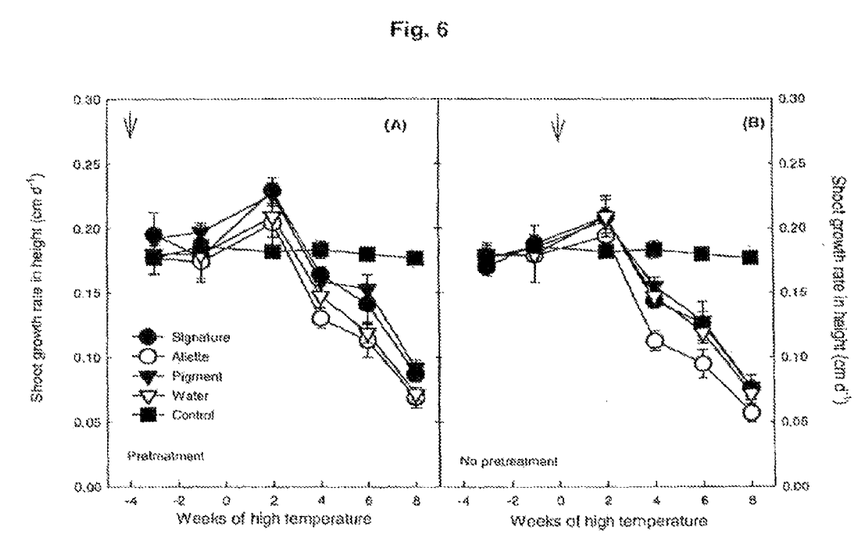
FIG. 6 illustrates the effect of phthalocyanine and fungicide applications on shoot growth rate in height of Penncross creeping bentgrass at high temperature treatment.

FIG. 6 illustrates the effect of fungicide application on shoot growth rate in height of Penncross creeping bentgrass at high temperature treatment. Data are shown as mean±sd. The arrow indicates the date of first fungicide application.

Shoot growth rate in canopy height increased in 2 weeks of high temperature treatment and then declined beginning 4 weeks after high temperature treatment in plants with and without pretreatment (FIGS. 6A and 6B). Shoot growth rate was higher with application of Signature fungicide and Pigment Green 7 than with application of Aliette fungicide and water for plants with and without pretreatment (FIGS. 6A and 6B). Growth rate was higher in plants with fungicide pretreatment than for those without pretreatment (FIGS. 6A and 6B).

G. Final Root and Canopy Biomass

Figure 7:
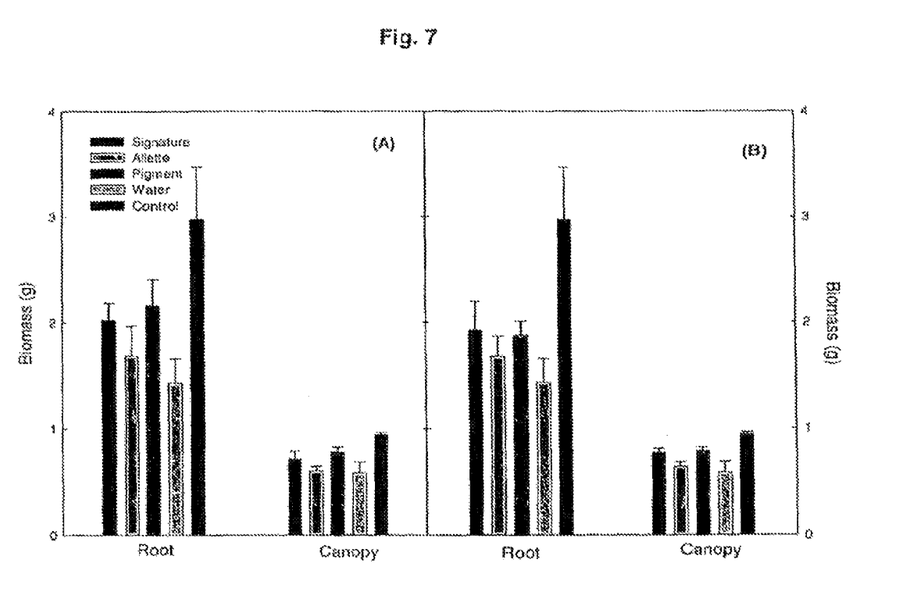
FIG. 7 illustrates the effect of phthalocyanine and fungicide applications on root and canopy shoot biomass of Penncross creeping bentgrass at high temperature treatment.

FIG. 7 illustrates the effect of fungicide application on root and canopy shoot biomass of Penncross creeping bentgrass at high temperature treatment. Data are shown as mean±sd.

High temperature treatment decreased both roots and canopy biomass (FIG. 7). Application of fungicide relieved the decline of roots and canopy biomass induced by heat stress (FIG. 7). Both roots and canopy biomass were higher with application of Signature fungicide and Pigment Green 7 than with application of Aliette fungicide and water for plants with and without fungicide pretreatment (FIGS. 7A and 7B). Plants with fungicide pretreatment had higher roots and canopy biomass than for those without pretreatment (FIGS. 7A and 7B).

H. Root Mortality

Figure 8:
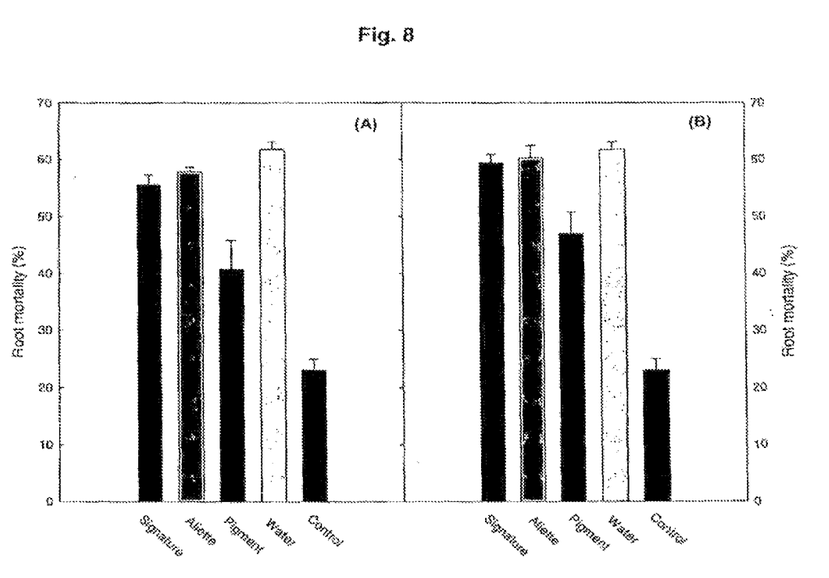
FIG. 8 illustrates the effect of phthalocyanine and fungicide applications on root mortality of Penncross creeping bentgrass at high temperature treatment.

FIG. 8 illustrates the effect of fungicide application on root mortality of Penncross creeping bentgrass at high temperature treatment. Data are shown as mean±sd.

Root mortality was increased by high temperature treatment (FIG. 8). Fungicide application reduced the increase of root mortality. Application of Pigment Green 7 produced lower root mortality than application of Signature fungicide and Aliette fungicide for plants with or without pretreatment (FIG. 8). Root mortality was lower for plants with pretreatment than for those without pretreatment (FIGS. 8A and 8B).

I. Tiller Density

Figure 9:
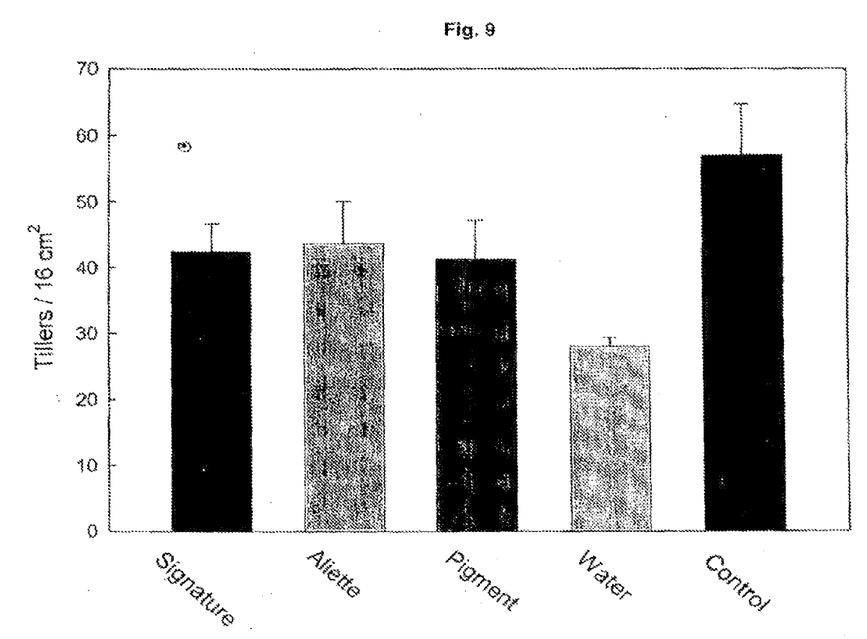
FIG. 9 illustrates the effect of phthalocyanine and fungicide application on tiller density of Penncross creeping bentgrass at high temperature treatment. In the figures the term "Pigment" refers to Pigment Green 7.

FIG. 9 illustrates the effect of fungicide application on tiller density of Penncross creeping bentgrass at high temperature treatment. Data are shown as mean±sd.

High temperature decreased tiller density. Applications of Signature fungicide and Aliette fungicide inhibited the decrease of tiller density induced by heat stress. There was no significant difference among applications of Signature fungicide, Aliette fungicide, and Pigment Green 7 (FIG. 9).

Example 2

Figure 10:
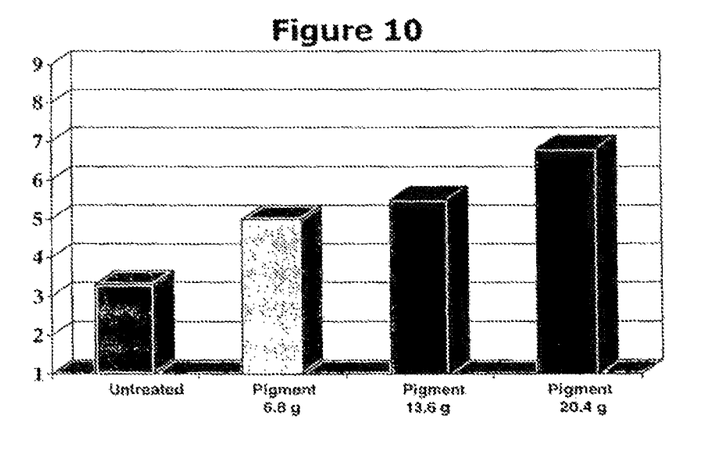
FIG. 10 illustrates the effect of phthalocyanine application on Penncross creeping bentgrass color.

Pigment Green 7 was suspended in water and applied as a foliar spray to creeping bentgrass (variety Penncross) turf with a pressurized sprayer at a spray volume of 1.37 gallons of water per 1000 sq. ft. (ca. 560 l/ha). Pigment Green 7 was applied at rates of 6.8, 13.9, and 20.4 grams per 1000 sq. ft. (0.73, 1.5, and 2.2 kg/ha, respectively). Each treatment was replicated 4 times. An untreated plot was included and was also replicated four times. The average color of the bentgrass was visually evaluated at 6 weeks after treatment. Color was evaluated on a qualitative scale from 1-9, with 9 being the highest quality and 1 the lowest quality. The color ratings with Pigment Green 7 treatments were significantly different than the untreated check based on analysis of variance. FIG. 10 shows the results of the trial.

Example 3

Fosetyl-al (in the form of Aliette brand fungicide), fosetyl-al plus Pigment Green 7 (in the form of Signature brand Aliette fungicide), and Pigment Green 7 were separately suspended in water and applied as a foliar spray to creeping bentgrass (variety Penncross) turf with a pressurized sprayer at a spray volume of 1.37 gallons of water per 1000 sq. ft. (ca. 560 l/ha).

Treatments were Applied at the Following Rates:

| | |
|---|---|
| Aliette | 4 oz/1000 sq. ft. (ca. 1.3 mL/m$^2$) |
| Signature | 4 oz/1000 sq. ft. (ca. 1.3 mL/m$^2$) |
| Signature | 8 oz/1000 sq. ft. (ca. 2.5 mL/m$^2$) |
| Pigment | 6.8 g/1000 sq. ft. (0.73 kg/ha) |
| Pigment | 13.6 g/1000 sq. ft. (1.5 kg/ha) |

Figure 11:
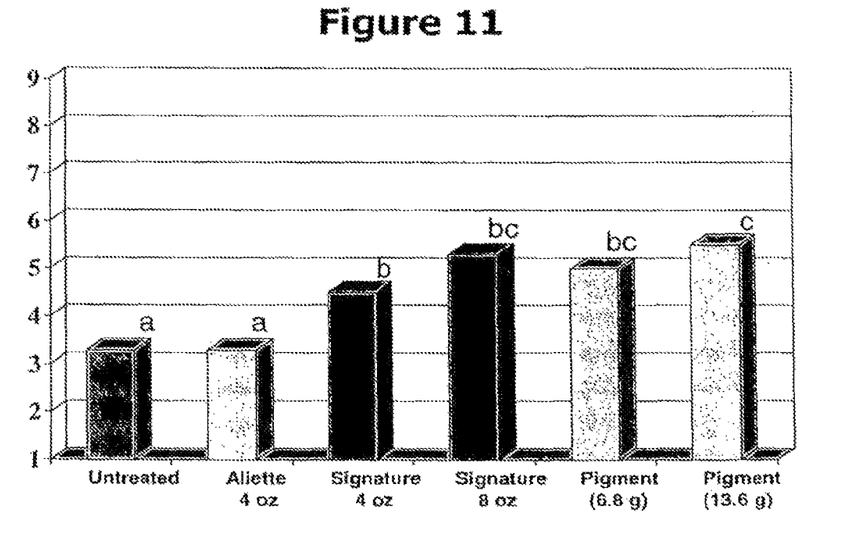
FIGS. 11 and 12 illustrate the effect of phthalocyanine and fungicide applications on the color of Penncross creeping bentgrass.

At 6 weeks after treatment, the color ratings were presented below. The color rating with Aliette and the untreated check were not significantly different. Pigment Green 7 and Signature treatments were significantly different than the untreated check based on analysis of variance. FIG. 11 shows the results.

Example 4

Figure 12:
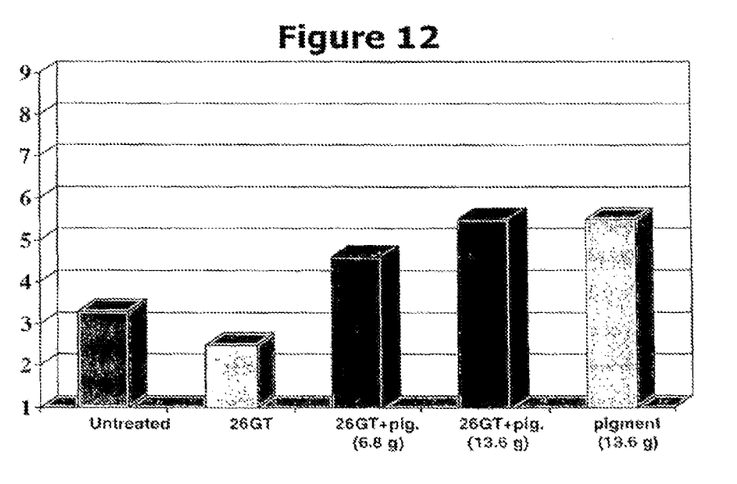

The procedure of Example 2 was repeated using iprodione fungicide (in the form of 26 GT brand iprodione fungicide) at 4 oz/1000 sq. ft. (ca. 1.3 mL/m$^2$), iprodione at 4 oz/1000 sq. ft. (ca. 1.3 mL/m$^2$) plus Pigment Green 7 at 6.8 g/1000 sq. ft. (0.73 kg/ha), iprodione at 4 oz/1000 sq. ft. plus Pigment Green 7 at 13.6 g/1000 sq. ft. (1.5 kg/ha), and Pigment Green 7 at 13.6 g/1000 sq. ft. (1.5 kg/ha). At 6 weeks after treatment, the color ratings were as follows. Turf treated with iprodione alone was not significantly different than the untreated check. Turf plots treated with iprodione plus Pigment Green 7 at both rates and Pigment Green 7 alone were significantly greener than the untreated. FIG. 12 shows the results.

Example 5

Example 1 is repeated except for using Pigment Blue 15 in each composition instead of Pigment Green 7.

Example 6

Example 2 is repeated except for using Pigment Blue 15 instead of Pigment Green 7.

Example 7

Example 3 is repeated except for using Pigment Blue 15 in each composition instead of Pigment Green 7.

Example 8

Example 4 is repeated except for using Pigment Blue 15 instead of Pigment Green 7.

Example 9

Studies carried out as a follow-up to Example 1 were conducted in 2005 to determine the influence of foliar applied phthalocyanine pigment on creeping bentgrass photosynthesis.

"Penncross" creeping bentgrass plants were grown in a growth chamber on a sand soil in PVC tubes (10 cm in diameter) maintained at 20° C. Plants were maintained at a canopy height of approximately 5 cm and a nutrient solution was applied weekly to maintain adequate fertility. Four plants were treated with Pigment Green 7 at a rate of 6.92 g/1000 sq. ft. (0.74 kg/ha) (with 0.6% Tween 20 being added to keep the pigment on the leaves for better absorption) and four plants were left untreated to serve as the controls (being sprayed with water only). Photochemical efficiency, chlorophyll content, and single leaf net photosynthesis were measured at one, three, seven, and fourteen days after application. Different light intensities of 1500, 750, 500, 250, 150, 50, and 0 µmol m$^{-2}$ s$^{-1}$ of photosynthetically active radiation (PAR, 400-700 nm) were generated inside the leaf chamber by an LED light source to generate a light response curve. Net photosynthesis was measured as the rate of $CO_2$ uptake (µmol m$^{-2}$s$^{-1}$). No differences in photochemical efficiency (Fv/Fm) between treated and control plants were observed, and no statistically significant differences in total chlorophyll per gram of tissue between treated and control plants were observed. At all light intensities greater than 50 µmol photons m$^{-2}$ s$^{-1}$ photosynthesis was higher for treated plants compared to controls. Photosynthesis was higher from the first day after application and all subsequent sampling dates. The light compensation point was unaltered by treatment. However at intensities of from 50 to 1500 µmol photons m$^{-2}$ s$^{-1}$ treated plants were more efficient in utilizing the constant amount of light produced in the leaf chamber. The higher net photosynthesis for treated plants on every date measured demonstrate that the phthalocyanine was stable for at least fourteen days after foliar application.

Example 10

A glasshouse study was conducted to determine the effect of soil drench applications of phthalocyanine pigment on corn growth and photosynthesis.

Corn was grown from seed in 6 inch (15 cm) pots in a potting soil mix. Pigment Green 7 was diluted in water in the four amounts per gallon (3.8 liter) of water indicated in the Table and applied directly to the soil. Treatments were initiated in March when corn was at the three leaf stage. Approximately 250 ml of the aqueous pigment mixture was applied to the soil on day 0 and day 6. On day 21 plants were placed in trays containing the pigment. Water was maintained in the trays as needed to replenished evapotranspiration.

Net photosynthesis of the youngest fully collared leaf (i.e., leaf 7) was measured using a LiCor 6400 instrument as µmol m$^{-2}$s$^{-1}$ of $CO_2$. Leaf chlorophyll measurements were made using a CM1000 leaf photosynthesis meter (Spectrum Technologies). Plant height, stem diameter, and leaf width were also measured at the end of the conclusion of the study. Results are shown in the following Table.

TABLE

| Pigment concentration (g/gal)[1] | Total height[2] (avg, cm) | Height soil to collar[3] (avg, cm) | Distance between collars[4] (avg, cm) | Leaf width[5] (avg, cm) | Stem diameter[6] (avg, cm) | Chlorophyl[7] | Net photo-synthesis[8] ($\mu$mol m$^{-2}$s$^{-1}$ of $CO_2$) |
|---|---|---|---|---|---|---|---|
| Untreated | 132 | 52 | 6.2 | 5.8 | 0.93 | 144 | 12.5 |
| 1 | 145 | 58 | 4.9 | 5.2 | 1.04 | 141 | 13.0 |
| 8 | 148 | 59 | 5.5 | 5.6 | 0.99 | 122 | 12.8 |
| 16 | 137 | 55 | 5.7 | 5.2 | 1.01 | 115 | 13.6 |
| 32 | 132 | 54 | 6.0 | 5.6 | 1.00 | 132 | 13.3 |

[1]Grams of pigment per gallon (3.8 liters) of water
[2]Measured from soil to youngest fully expanded leaf tip
[3]Measured from soil to collar of youngest fully expanded leaf tip
[4]Distance between two top collars
[5]Leaf width at widest part of the first fully expanded leaf
[6]Diameter measured on the wide area of the stem directly under youngest fully expanded leaf
[7]Three chlorophyll readings around center of youngest fully expanded leaf (3 plants per pot)
[8]Measured on youngest fully collared lea

What is claimed is:

1. A method of improving quality of grass under stress comprising applying to grass a composition comprising an amount of a phthalocyanine effective to improve the quality of grass under stress, wherein
   (i) the composition does not include phosphorous acid or a salt thereof or a monoalkyl ester of phosphorous acid or a salt thereof;
   (ii) about 0.01 to about 2 kg per hectare of said phthalocyanine is applied to said grass; and wherein the application of said composition to grass improves the quality of grass under stress
   (iii) wherein said phthalocyanine is a copper phthalocyanine, and
   (iv) said composition does not include a metallic ethylene bisdithiocarbamate contact fungicide.

2. The method according to claim 1, wherein
   (v) the composition does not include an effective amount of other fungicides.

3. The method of claim 1, comprising applying to grass an effective amount of a composition comprising from 1% to 95% by weight of the copper phthalocyanine on a solid support, from 0 to 5% by weight of a wetting agent, and from 3 to 10% by weight of a dispersant.

4. The method of claim 1, wherein said composition does not include a polymer.

5. The method of claim 1, wherein about 0.1 to about 1 kg per hectare of said phthalocyanine is applied to grass.

6. The method of claim 1, wherein said stress is heat induced stress.

7. A method of improving quality of grass under stress comprising applying to grass a composition comprising an amount of a phthalocyanine effective to improve the quality of grass under stress, wherein
   (i) the composition does not include phosphorous acid or a salt thereof or a monoalkyl ester of phosphorous acid or a salt thereof;
   (ii) about 0.01 to about 2 kg per hectare of said phthalocyanine is applied to said grass; and wherein application of said composition to said grass improves the quality of the grass under stress
   (iii) wherein said phthalocyanine is selected from the group consisting of Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7, and
   (iv) said composition does not include a metallic ethylene bisdithiocarbamate contact fungicide.

8. The method of claim 7, wherein about 0.1 to about 1 kg per hectare of said phthalocyanine is applied to grass.

9. The method of claim 7, wherein said stress is heat induced stress.

10. A method of improving quality of grass under stress comprising applying to grass a composition comprising an amount of a phthalocyanine effective to improve the quality of grass under stress, wherein
    (i) the composition does not include phosphorous acid or a salt thereof or a monoalkyl ester of phosphorous acid or a salt thereof;
    (ii) about 0.01 to about 2 kg per hectare of said phthalocyanine is applied to said grass; and wherein the application of said composition to grass improves the quality of grass under stress
    (iii) wherein said composition comprises a fungicide, wetting agent, dispersant, and stabilizer, and
    (iv) said composition does not include a metallic ethylene bisdithiocarbamate contact fungicide.

11. The method of claim 10, wherein about 0.1 to about 1 kg per hectare of said phthalocyanine is applied to grass.

12. The method of claim 10, wherein said stress is heat induced stress.

* * * * *